(12) United States Patent
Siess et al.

(10) Patent No.: US 12,296,134 B2
(45) Date of Patent: *May 13, 2025

(54) SHEATH FOR SEALED ACCESS TO A VESSEL

(71) Applicant: Abiomed Europe Gmbh, Aachen (DE)

(72) Inventors: Thorsten Siess, Aachen (DE); Christoph Nix, Aachen (DE); Frank Kirchhoff, Aachen (DE); Patrick Hunziker, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 578 days.

This patent is subject to a terminal disclaimer.

(21) Appl. No.: 17/108,781

(22) Filed: Dec. 1, 2020

(65) Prior Publication Data

US 2021/0146109 A1 May 20, 2021

Related U.S. Application Data

(63) Continuation of application No. 15/323,504, filed as application No. PCT/EP2015/065292 on Jul. 6, 2015, now Pat. No. 10,881,845.

(30) Foreign Application Priority Data

Jul. 4, 2014 (EP) ..................................... 14175795

(51) Int. Cl.
*A61M 39/02* (2006.01)
*A61M 39/06* (2006.01)
(Continued)

(52) U.S. Cl.
CPC .... *A61M 39/0247* (2013.01); *A61M 39/0606* (2013.01); *A61M 60/135* (2021.01);
(Continued)

(58) Field of Classification Search
CPC ........ A61M 39/02; A61M 39/06; A61M 1/12; A61M 5/14276; A61M 39/0247;
(Continued)

(56) References Cited

U.S. PATENT DOCUMENTS 4,540,411 A 9/1985 Bodicky
4,699,611 A 10/1987 Bowden
(Continued)

FOREIGN PATENT DOCUMENTS

CN 1501825 A 6/2004
CN 2699842 Y 5/2005
(Continued)

OTHER PUBLICATIONS

Office Action for corresponding JP Application No. 2021-121210 dated Jun. 23, 2022, (11 pages).
(Continued)

*Primary Examiner* — Anu Ramana
(74) *Attorney, Agent, or Firm* — Botos Churchill IP Law

(57) ABSTRACT

A sheath for producing a fully sealed access to the interior of a vessel of an animal or human body comprises a base sheath having a tubular body defining a pass-through channel. The base sheath is adapted to be inserted into the vessel through a vessel aperture. A wall of the tubular body of the base sheath has a through channel. This channel extends in the wall from the distal end towards the proximal end. The channel can be present separately from the pass-through channel of the base sheath or can form a sideways extension of the pass-through channel, at least at the distal end. Such through channel is adapted to conduct blood from the vessel to the proximal end of the sheath when the sheath has been inserted into a vessel.

19 Claims, 2 Drawing Sheets

(51) Int. Cl.
- *A61M 60/135* (2021.01)
- *A61M 60/268* (2021.01)
- *A61M 60/148* (2021.01)
- *A61M 60/414* (2021.01)
- *A61M 60/857* (2021.01)

(52) U.S. Cl.
CPC ... *A61M 60/268* (2021.01); *A61M 2039/0258* (2013.01); *A61M 2039/0267* (2013.01); *A61M 2039/0273* (2013.01); *A61M 2039/0279* (2013.01); *A61M 2039/062* (2013.01); *A61M 2039/0626* (2013.01); *A61M 2039/0633* (2013.01); *A61M 60/148* (2021.01); *A61M 60/414* (2021.01); *A61M 60/857* (2021.01); *A61M 2205/32* (2013.01); *A61M 2205/3344* (2013.01); *A61M 2205/6063* (2013.01); *A61M 2230/30* (2013.01); *A61M 2230/50* (2013.01)

(58) Field of Classification Search
CPC .. A61M 2039/0232; A61M 2039/0241; A61M 2039/0045; A61M 2039/0202; A61M 2039/0205
See application file for complete search history.

(56) References Cited

U.S. PATENT DOCUMENTS

| | | |
|---|---|---|
| 4,769,005 A | 9/1988 | Ginsburg et al. |
| 4,881,542 A | 11/1989 | Schmidt et al. |
| 5,139,486 A | 8/1992 | Moss |
| 5,234,425 A | 8/1993 | Fogarty et al. |
| 5,304,142 A | 4/1994 | Liebl et al. |
| 5,320,611 A | 6/1994 | Bonutti et al. |
| 5,360,397 A | 11/1994 | Pinchuk |
| 5,395,341 A | 3/1995 | Slater |
| 5,397,310 A | 3/1995 | Chu et al. |
| 5,407,430 A | 4/1995 | Peters |
| 5,413,571 A | 5/1995 | Katsaros et al. |
| 5,413,574 A | 5/1995 | Fugo |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,653,697 A | 8/1997 | Quiachon et al. |
| 5,676,689 A | 10/1997 | Kensey et al. |
| 5,766,151 A | 6/1998 | Valley et al. |
| 5,911,702 A | 6/1999 | Romley et al. |
| 5,935,122 A | 8/1999 | Fourkas et al. |
| 5,971,993 A | 10/1999 | Hussein et al. |
| 6,022,319 A * | 2/2000 | Willard ............. A61M 25/0026 600/470 |
| 6,090,072 A | 7/2000 | Kratoska et al. |
| 6,197,016 B1 | 3/2001 | Fourkas et al. |
| 6,338,730 B1 | 1/2002 | Bonutti et al. |
| 6,413,235 B1 | 7/2002 | Parodi |
| 6,428,556 B1 | 8/2002 | Chin |
| 6,613,038 B2 | 9/2003 | Bonutti et al. |
| 6,626,918 B1 | 9/2003 | Ginn et al. |
| 6,692,462 B2 | 2/2004 | Mackenzie et al. |
| 6,733,515 B1 | 5/2004 | Edwards et al. |
| 6,814,715 B2 | 11/2004 | Bonutti et al. |
| 7,022,100 B1 | 4/2006 | Aboul-Hosn et al. |
| 7,025,746 B2 | 4/2006 | Tal |
| 7,722,567 B2 | 5/2010 | Tal |
| 8,382,793 B2 | 2/2013 | Egneloev et al. |
| 8,597,277 B2 | 12/2013 | Lenker et al. |
| 8,672,888 B2 | 3/2014 | Tal |
| 8,758,402 B2 | 6/2014 | Jenson et al. |
| 2004/0015061 A1 | 1/2004 | Currier et al. |
| 2004/0138674 A1 | 7/2004 | Egnelov et al. |
| 2004/0176798 A1 | 9/2004 | Foy et al. |
| 2005/0107750 A1 | 5/2005 | Barongan |
| 2005/0149105 A1 | 7/2005 | Leeflang et al. |
| 2005/0267522 A1 | 12/2005 | Yassinzadeh et al. |
| 2006/0135981 A1 | 6/2006 | Lenker et al. |
| 2006/0287574 A1 | 12/2006 | Chin |
| 2007/0016106 A1 | 1/2007 | Ramaiah et al. |
| 2007/0088317 A1 | 4/2007 | Hyde |
| 2007/0293754 A1 | 12/2007 | Schneid et al. |
| 2008/0009828 A1 | 1/2008 | Miller et al. |
| 2008/0021382 A1 | 1/2008 | Freyman |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0076959 A1* | 3/2008 | Farnan ............. A61M 25/0662 604/165.01 |
| 2008/0082165 A1 | 4/2008 | Wilson et al. |
| 2008/0125707 A1 | 5/2008 | Wilson et al. |
| 2008/0132980 A1* | 6/2008 | Gerber ................ A61N 1/0534 607/116 |
| 2009/0069786 A1 | 3/2009 | Vesely et al. |
| 2009/0105545 A1 | 4/2009 | Janis et al. |
| 2009/0137968 A1 | 5/2009 | Rottenberg |
| 2009/0177225 A1 | 7/2009 | Nunez et al. |
| 2009/0240202 A1 | 9/2009 | Drasler et al. |
| 2010/0185058 A1 | 7/2010 | Mastri et al. |
| 2012/0053611 A1 | 3/2012 | Saab et al. |
| 2012/0296275 A1 | 11/2012 | Martin et al. |
| 2013/0131718 A1 | 5/2013 | Jenson et al. |
| 2013/0317438 A1 | 11/2013 | Ellingwood et al. |
| 2013/0317481 A1 | 11/2013 | Ellingwood et al. |
| 2014/0121670 A1 | 5/2014 | Bishop et al. |
| 2014/0276742 A1 | 9/2014 | Nabutovsky et al. |
| 2014/0303596 A1 | 10/2014 | Schumacher et al. |
| 2016/0066948 A1 | 3/2016 | Ellingwood et al. |
| 2016/0220358 A1 | 8/2016 | Wilson et al. |
| 2016/0354583 A1 | 12/2016 | Ellingwood et al. |
| 2017/0056063 A1 | 3/2017 | Ellingwood et al. |
| 2017/0281908 A1 | 10/2017 | Ellingwood et al. |

FOREIGN PATENT DOCUMENTS

| | | |
|---|---|---|
| CN | 1835715 A | 9/2006 |
| CN | 102892455 A | 1/2013 |
| CN | 106659826 A | 5/2017 |
| CN | 106659877 A | 5/2017 |
| DE | 102008058864 A1 | 5/2010 |
| EP | 0363203 A2 | 4/1990 |
| EP | 2233169 A1 | 9/2010 |
| JP | H02102670 A | 4/1990 |
| JP | H06190053 A | 7/1994 |
| JP | H06510462 A | 11/1994 |
| JP | H08500518 A | 1/1996 |
| JP | 2013013446 A | 1/2013 |
| WO | 9112836 A1 | 9/1991 |
| WO | 9308746 A2 | 5/1993 |
| WO | 9640347 A1 | 12/1996 |
| WO | 2004007012 A2 | 1/2004 |
| WO | 2005016152 A2 | 2/2005 |
| WO | 2005102005 A1 | 11/2005 |
| WO | 2008014358 A2 | 1/2008 |

OTHER PUBLICATIONS

Office Action issued in corresponding Chinese Patent Application No. 201580036594.4 dated Jun. 3, 2021, 11 pp.

Office Action issued in corresponding Japanese Patent Application No. 2020-116214 dated Apr. 27, 2021 (10 pages).

International Search Report and Written Opinion dated Sep. 29, 2015 for International Application No. PCT/US2015/065290, filed Jul. 6, 2015.

International Search Report and Written Opinion dated Sep. 29, 2015 for International Application No. PCT/US2015/065292, filed Jul. 6, 2015.

Advisory Action issued in U.S. Appl. No. 15/323,660 dated Nov. 3, 2020.

Final Office Action issued in U.S. Appl. No. 15/323,660 dated Jul. 10, 2020.

Non final Office Action issued in U.S. Appl. No. 15/323,660 dated Dec. 21, 2020.

(56) References Cited

OTHER PUBLICATIONS

Non-final Office Action issued in U.S. Appl. No. 15/323,660 dated Nov. 22, 2019.
Non final Office Action issued in corresponding U.S. Appl. No. 15/323,660 dated Jan. 25, 2022 (16 pages).
Office Action issued in corresponding Korean Patent Application No. 10-2017-7003164 dated Sep. 27, 2021 (15 pages).
Office Action issued in corresponding Chinese Patent Application No. 202010313711.X dated Sep. 14, 2021 (30 pages).
Office Action issued in corresponding Korean Patent Application No. 10-2017-7003160 dated Sep. 27, 2021 (14 pages).
Japanese Office Action issued in corresponding Japanese Patent Application No. 2019-210072 dated Dec. 8, 2020, 8 pp.
Office Action issued in Korean Patent Application No. 10-2022-7027140 dated Nov. 25, 2022 (12 pp).
Office Action issued in corresponding Japanese Patent Application No. 2021-149915 dated Aug. 23, 2022, 4 pages.
Office Action from corresponding Korean Patent Application No. 10 2022-7038598 dated Aug. 30, 2023 (17 pp.).
CN Office Action dated Oct. 27, 2023 for CN Appln. No. 202110110026.1.

* cited by examiner

SHEATH FOR SEALED ACCESS TO A VESSEL

CROSS REFERENCE TO RELATED APPLICATION

This application is a continuation of U.S. patent application Ser. No. 15/323,504 filed Jan. 3, 2017, now U.S. Pat. No. 10,881,845, which is a National Stage of International Application No. PCT/EP2015/065292, filed Jul. 6, 2015, which claims priority to European Patent Application No. 14175795.5, filed Jul. 4, 2014, the contents of which are incorporated by reference herein in their entireties.

TECHNICAL FIELD

The present invention relates to a sheath for producing a fully sealed access to the interior of a vessel of an animal or human body, for example an artery.

BACKGROUND OF THE INVENTION

Sheaths are employed in different forms during percutaneous interventions on the human body, for example when introducing a heart catheter via an artery or vein, for example the femoral artery. Different steps of such an intervention will be set forth hereinafter in a brief and simplified form to lead up to the object of the invention.

In a first phase, the vessel is punctured for this purpose with a puncture needle. Through this needle a first guidewire is then inserted into the vessel. The needle is removed and a first sheath is inserted into the vessel along the guidewire. The above steps are carried out according to the well-known "Seldinger technique". This sheath normally comprises a base sheath, a removable dilator and a hemostatic valve at the proximal end of the sheath, i.e. at the end of the sheath facing the practitioner's body. In connection with the present invention the anatomical direction terms will be chosen with reference to the practitioner. The sheath possesses an outer diameter of about 2 mm. The dilator and the guidewire are successively removed, so that only the base sheath of the first sheath remains partially in the vessel.

In a second phase, a stiff guidewire is now inserted into the vessel through the remaining base sheath, for example up to a depth of 40 cm. Thereafter the base sheath is removed. The guidewire remains partially in the vessel.

Optionally this can be followed by a further pre-dilation, which shall not be described here. Optionally or alternatively, instead of applying a small intermediary sheath, the puncture into the vessel can be up-dilated by applying various sizes of dilators over the originally deployed guidewire.

Along the guidewire remaining in the vessel, that sheath is now inserted into the vessel through which the heart pump is to be introduced. In the context of the present application, an "introducer" or an "introducing sheath" is a sheath having a hemostatic valve. This introducing sheath normally possesses an inner diameter of from about 4.5 to 5 mm and an outer diameter of from about 5 to 6 mm. The basic structure of the introducing sheath is identical to the structure of the above-mentioned first sheath, i.e. it consists of an outer base sheath, a dilator and a hemostatic valve. Dilator and guidewire are removed again, with the base sheath of the introducing sheath remaining in the blood vessel. The access for the heart pump has now been created.

Through the base sheath a guide catheter is now normally placed along the artery into the left ventricle. For this purpose, there can be employed for example a so-called pigtail catheter, which consists of a thin tube and a soft distal precurved guiding tip. A supporting guidewire may already be inserted into the guide catheter extending therein, which supports the catheter. Said soft, supporting wire is thereafter removed, and a harder guidewire is inserted into the heart through the catheter. Along the hard guidewire the heart pump is inserted into the heart, after removal of the pigtail catheter. The inlet of the heart pump is then located in the left ventricle, the outlet in the aorta and the guidewire is retrieved. The pump is connected to a supply catheter which extends along the artery employed for placing the pump and which exits at the vessel aperture (puncture side). Alternatively, the pump can directly be inserted into the base sheath and can be delivered into the heart without the need for additional guide catheters and guidewires in case the pump has been designed with the appropriate features necessary to retrogradely pass the aortic valve in a trauma free manner.

The introducing sheath that has been employed for inserting the heart pump is now removed from the vessel and pulled out completely before final removal is performed, for example by splitting along a predetermined separating line ("peel-away" technique). To now close the vessel at the vessel aperture again, i.e. to close the gap between the circumference of the hole in the vessel and the outer diameter of the supply catheter of the pump, a further sheath is inserted into the vessel along that portion of the heart-pump supply catheter that is located outside the body. The last-mentioned sheath is the subject matter of the present invention. Because it is also possible to displace or reposition the heart pump through this sheath, for example via the supply catheter, the sheath is also called a repositioning sheath (or "repo sheath").

To avoid a blood flow disturbance in the artery and potential low flow or foreign surface related thrombosis, the sheath should only be inserted into the vessel as deep as necessary and have an outer diameter just sufficient to close the vessel in a fully sealed manner, i.e. to stop bleeding or oozing that would otherwise occur.

It is hence desirable to be able to reliably recognize whether and when the sheath has been inserted deep enough into the vessel. This can vary depending on the thickness of the subcutaneous fatty tissue to be penetrated and/or the angulation of the access and hence be difficult to determine.

SUMMARY OF THE INVENTION

The object of the present invention is therefore to propose a sheath that enables recognition of a sufficient penetration depth.

This object is achieved by a sheath and a method having the features of the independent claims. Advantageous embodiments and developments are stated in the dependent claims.

The sheath comprises for this purpose a base sheath having a tubular body defining a pass-through channel. Normally the sheath comprises a conventional hemostatic valve at the proximal end. The base sheath is adapted to be inserted into the vessel through a vessel aperture, i.e. to be installed in the vessel through the vessel aperture.

To enable recognition of the penetration depth, a wall of the tubular body of the base sheath has a through channel. This through channel extends in the wall from the distal end towards the proximal end. The through channel may exit the wall of the tubular body to the outside of the sheath at the proximal end of the sheath or earlier, i.e. between the distal end and the proximal end of the sheath. The through channel can be present separately from the pass-through channel of the base sheath. According to an alternative embodiment, the through channel can be formed as a sideways extension of the pass-through channel, at least at the distal end, i.e. it has not to be separate from the pass-through channel over its entire length. Such through channel is adapted to conduct blood from the vessel to the proximal end of the sheath when the sheath has been inserted into a vessel. In this way one can reliably see as soon as the sheath has been inserted into the vessel through the tissue at sufficient depth. In other words, the channel enables a kind of insertion depth indicator to be obtained, simply by the fact that as soon as blood from the vessel becomes recognizable at the proximal end of the channel, a sufficiently deep insertion of the sheath into the vessel can be inferred. There is in particular no danger of the sheath being inserted further into the vessel than necessary, which could otherwise cause blood flow disturbances.

Advantageously, blood can also be taken for diagnostic purposes through the channel in a suitable manner. Significant diagnostic methods here are in particular measurement of the patient's blood pressure and a determination of the cardiac output. For measuring blood pressure, the sheath can further comprise a blood pressure measuring device which is connected to the channel. The cardiac output can be determined for example by means of thermodilution. For this purpose, the sheath can comprise a temperature measuring element, for example a thermistor, inserted through the channel.

The sheath can further comprise a guidewire which is preferably installable through the channel. In other words, the channel is then adapted to insert the guidewire into the vessel from the proximal end of the sheath via the channel. Via such a guidewire vessel access is maintained even after withdrawal of the pump.

According to a preferred embodiment, the sheath comprises an expansion device. The latter is adapted to cooperate with the base sheath such that the outer diameter of the sheath increases in the region of the vessel aperture with the sheath in a stationary position in the vessel and upon actuation of the expansion device.

For producing a fully sealed access to a vessel by means of this embodiment of the sheath, the sheath is therefore inserted into the vessel through the vessel aperture. Thereafter the outer diameter of the sheath is increased as needed in the region of the vessel aperture through actuation of the expansion device of the sheath.

To increase the outer diameter of the sheath in case of need, it is unnecessary to insert the sheath deeper into the vessel, because an increase of the outer diameter of the sheath in the region of the vessel aperture is possible with the sheath in a stationary position. Since the sheath has a relatively small outer diameter in its initial state, i.e. without actuation of the expansion device, one can avoid an unnecessary widening of the vessel aperture as well as a blood flow disturbance in the vessel due to a large outer diameter or long penetration depth.

It is intended to design the repositioning sheath so that it is initially undersized, e.g. the initial outer diameter of the sheath can be up to 4 F (=1.33 mm) smaller in diameter as compared to the initial puncture diameter created by the introducing sheath for the pump. The reason for this undersized outer diameter is that the vessel itself may have the ability to recoil elastically to a smaller hole if the initial larger sheath is placed only for a short period (<60 min). It will be appreciated that the smallest obdurator which achieves hemostasis is the most preferred embodiment with the least amount of foreign material in the vessel and the smallest likelihood of full vessel obstruction and discontinued distal perfusion. Only in case of no or limited vessel recoil the expanding portion of the repositioning sheath will be expanded gradually in order to obtain hemostasis. In a preferred embodiment the expanding device is configured such that an expanding portion of the sheath is confined to the target area around the vessel puncture allowing for the proximal sheath, which extends through the skin to the outside of the body, to be recessed. In this way, bleeding would still be visible at the skin level requiring a further expansion of the expanding portion. Henceforth, it is less likely to plug the puncture at the skin level and potentially have continuous bleeding at the vessel puncture into the adjacent tissue, which would later show up as a circular hematoma.

According to a further preferred embodiment, the expansion device is configured as an expansion sheath displaceable on the sheath in the direction of the vessel aperture. Such expansion sheath can for example tubularly encompass the base sheath. By displacing the expansion sheath on the base sheath in the direction of the vessel aperture, one can increase the outer diameter of the sheath in the region of the place of entry into the vessel, without inserting the sheath as a whole deeper into the vessel.

A plurality of embodiments of an expansion device that diverge from the above are possible. For example, an expansion device can be provided that is not displaced on the base sheath in the direction of the vessel aperture, but that is arranged in the pass-through channel of the base sheath or around the base sheath. Such an expansion device can basically be structured like a dilator and for example widen the base sheath, or a sleeve arranged on the base sheath (to be described more exactly hereinafter), from the inside, for example like a balloon dilator. The balloon dilator can also be arranged on the outside of the sheath. According to a preferred embodiment, an expansion device in the form of a spiral inflation tube is provided, which is preferably arranged between the base sheath and the sleeve. The inflation tube is spirally wound around the base sheath. During inflation of the tube, the sheath is expanded while still being flexible, i.e. bendable, in the expanded area.

Instead of a balloon dilator or the like there can also be provided a mechanical spreading element, for example a wire mesh-like stent. Such a spreading element can be brought from a contracted to an expanded position, for example by rotation or displacement of an actuating element arranged at the proximal end of the sheath and coupled with the spreading element, so that the outer diameter of the sheath increases in the region of the spreading element. According to a preferred embodiment, the sheath comprises a flexible portion in the area to be expanded. This flexible portion forms a part of the base sheath and is arranged between the proximal end and the distal end. The flexible portion can be expanded by operating a pulling means which is connected to the base sheath at the distal end.

According to a further preferred embodiment, the sheath comprises, as an expansion device, a stretchable portion in the area to be expanded. This stretchable portion forms part of the base sheath and is arranged between the proximal end and the distal end. The stretchable portion is configured to attain a first thickness in a stretched condition and a second thickness, which is larger than the first thickness, in an unstretched condition, so as to increase the outer diameter of the sheath when the proximal end portion of the base sheath is released in direction of the vessel aperture from the stretched condition to the unstretched condition. In other words, the sheath having the stretchable portion offers the smallest outer diameter in a stretched condition. By releasing the stretching—from the proximal end of the sheath in direction of the vessel aperture—the stretchable portion attains an unstretched condition which results in a larger outer diameter of the sheath in the area of the vessel aperture. This embodiment is advantageous in case the sheath has a minimum wall thickness that precludes a uniform compression by axial displacement.

An arbitrary other form of analogous spreading, expanding or widening apparatus can be provided as an expansion device. In just another embodiment the expansion can be automated by swelling a material with the surrounding blood (e.g. a hydrophilic gel), which only expands gently to the "right size" with minimal stress to the vessel by appropriate choice of the swelling modulus.

According to a further preferred embodiment, the sheath comprises a sleeve, as already indicated. The sleeve encases the base sheath and the expansion device such that the sleeve is in contact with the vessel aperture when the sheath has been inserted into the vessel, i.e. with the sheath in a stationary position in the vessel. This can prevent a traumatic effect of the expansion device on the vessel when the expansion device is actuated, in particular advanced, for increasing the outer diameter of the sheath. This sleeve serves as well as a sterile barrier and allows the insertion of non sterile expanders from the proximal end of the repositioning sheath.

In case the expansion device is configured in the form of the hereinabove described expansion sheath that is displaceable on the base sheath, the sleeve encases the base sheath and the expansion sheath such that the expansion sheath is displaceable on the base sheath between the base sheath and the sleeve.

Preferably, the base sheath has a pass-through channel having an inner diameter through which a catheter, preferably a supply catheter of a heart pump, can be guided. An inner diameter of about 3 mm may be sufficient for this purpose. It will be appreciated that the inner diameter of the sheath can be adjusted in accordance with the intended application and can also be paired and operated with any other indwelling device.

Preferably, the outer diameter of the sheath is chosen sufficiently large that a vessel aperture arising upon insertion of a heart pump through the vessel is closed in a fully sealed manner, ideally without actuation of the optional expansion device. An outer diameter of about 3.33 mm to 5 mm is sufficient for this purpose in view of currently employed heart pumps and introducing sheaths for introducing the pumps. It will be appreciated that the outer diameter of the sheath can also be adjusted, i.e. reduced or increased, in view of the application. But it shall be mentioned that vascular complication rates exponentially increase above 5 mm, which is why the preferred target size should aim at the smallest possible diameter which achieves hemostasis.

The expansion device of the sheath is preferably adapted to increase the outer diameter of the sheath in the region of the vessel aperture by about 1 F to 3 F (0.33 mm to 1.00 mm), preferably by about 1 F to 4 F (0.33 mm to 1.33 mm), particularly preferably by about 1 F to 5 F (0.33 mm to 1.66 mm). In this way it can be ensured that a fully sealed access to the interior of the vessel is produced in different scenarios, in particular in view of different patients with different vessel recoil potential and vessel sizes.

Further to having a correct sealing diameter, it is equally important that an expanding portion of the sheath is "radially soft". In this context, radially soft means that this portion must not act like a stiff portion, which can distort and/or traumatize the vessel, but that this portion can still confine to the curvature/radius at which the repositioning sheath enters into the vessel. This mandates low durometer polymeric materials and/or a special design of the expansion device, e.g. a helically wound inflation tube (already mentioned above). The latter can radially expand, but will not exceed any tangential force causing the pre-curved portion to stretch longitudinally or stretch out.

The degree of expansion of the outer diameter of the sheath is either guided by the inflation pressure of a balloon or any other means of force feedback that could be used to limit the expansion to a diameter sufficient to provide hemostasis. An expanding force slightly above the maximum blood pressure is considered to be sufficient. The expanding force can be considered equal to the inflation pressure of a balloon if the balloon material is highly compliant.

According to a further preferred embodiment, the sheath comprises a fixation element at the proximal end. Said fixation element serves for fixing the sheath to a patient after insertion of the sheath into the patient's vessel. The fixation element can thus be stitched to the patient's skin, for example. The fixation element comprises an area spanning the base sheath for applying a sterile cover. The area slopes down in a ramp shape on both sides of the base sheath transversely to the principal direction of the base sheath.

Such an embodiment of the fixation element allows a simple and safe application of the sterile cover and thereby minimizes the places of entry for germs and pathogens at the vessel aperture.

The fixation element can additionally comprise a fixation area which lies on the patient's skin in the fixed state. The fixation area is then located opposite the above-mentioned area for applying the sterile cover.

Preferably, the fixation element further comprises a guide element. Said guide element serves as a stop for applying the sterile cover. Preferably, the guide element extends at the proximal end of the area transversely to the principal direction of the base sheath and substantially perpendicular to the area, but at least so as to protrude from the area such that the functionality of a stop can be provided. Through the application of the sterile cover on the guide element and through the configuration of the smooth area for wrinkle-free application of the sterile cover there can be obtained an especially safe and sterile covering of the wound. The guide element also helps to prevent an inadvertent fixation of any elements of the repositioning sheath proximal of the fixation element such as the anti-contamination sleeve used to protect the proximal parts of the catheter from contamination.

According to a further preferred embodiment, the sheath comprises a heart pump having a supply catheter. The sheath is here adapted to be arranged displaceably on the supply catheter. In other words, heart pump, supply catheter and sheath form a cohesive system according to this embodiment.

BRIEF DESCRIPTION OF THE DRAWINGS

Hereinafter the invention will be described by way of example with reference to the attached drawings. Therein are shown.

DETAILED DESCRIPTION

Figure 1:
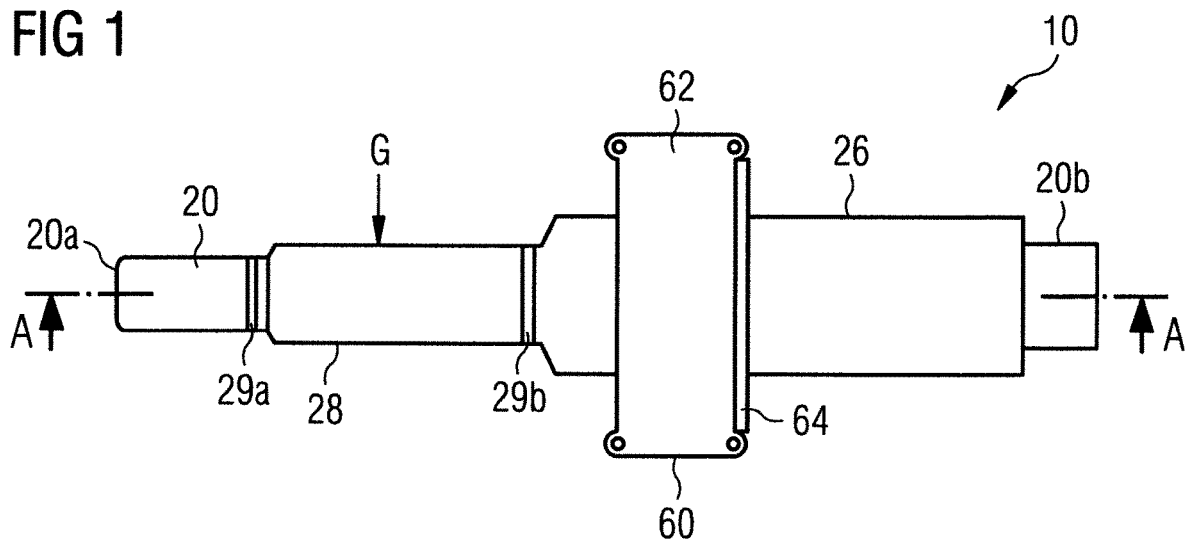
FIG. 1 a preferred embodiment of a sheath according to the invention in a plan view.
Figure 2:
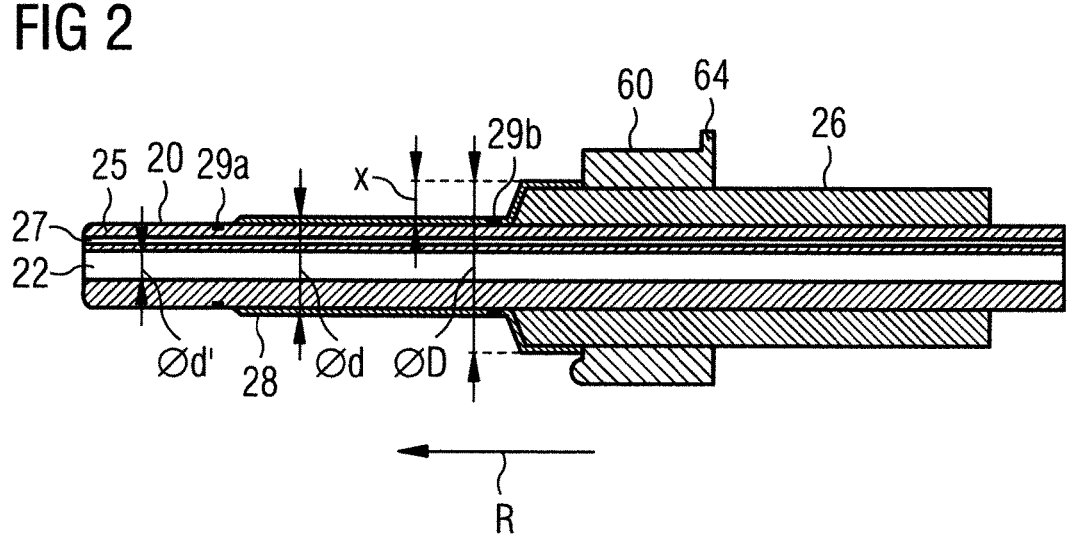
FIG. 2 the sheath from FIG. 1 in a lateral sectional view.
Figure 3:
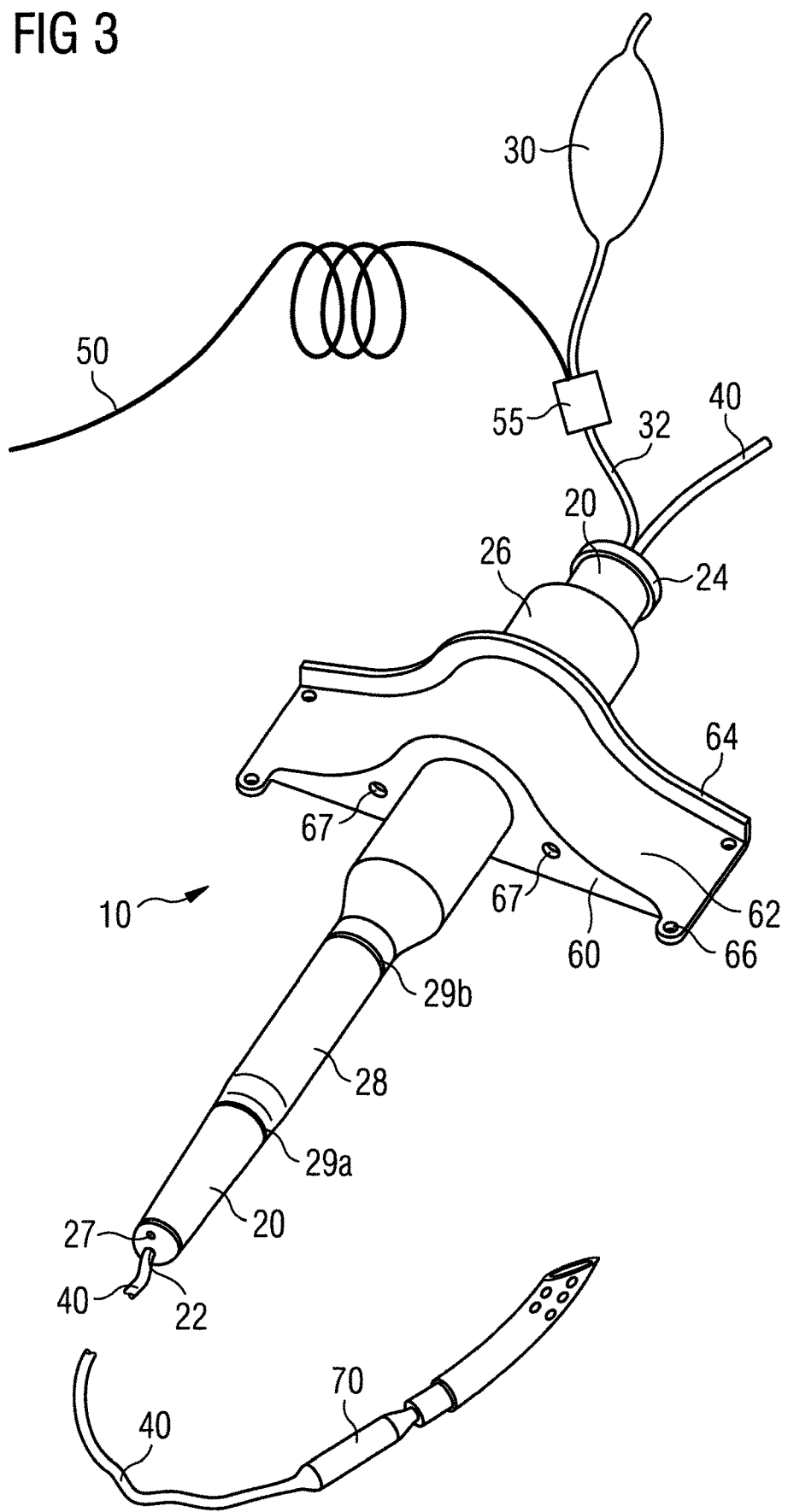
FIG. 3 the sheath from FIG. 1 in a perspective view together with further, optional sheath elements.

The representation of the sheath 10 in FIGS. 1 to 3 is not true to scale, but only schematic. For better illustrating some elements of the sheath 10, the actual size relations are thus occasionally incorrect. E.g. tapered portions are exaggerated looking more like slanted steps rather than a gentle and smooth transition from the smaller to the larger diameter.

As shown in FIGS. 1 and 2, the sheath 10 serving to produce a fully sealed access to the interior of a vessel of an animal or human body comprises a base sheath 20 having a tubular body defining a pass-through channel 22. A hemostatic valve 24 (cf. FIG. 3) terminates the sheath at the proximal end 20b.

The pass-through channel 22 has an inner diameter d' and an outer diameter d. The inner diameter d' is dimensioned such that the sheath 10 is suitable to be pushed over a supply catheter 40 of a heart pump 70 (compare FIG. 3) and preferably amounts to about 3 mm. The outer diameter d preferably amounts to about 3.33 mm to 5 mm, so that the sheath 10 is suitable for closing in a fully sealed manner a vessel aperture arising upon insertion of the introducer of the heart pump 70 through the vessel. The outer diameter d may need to be larger than 3.33 mm, based e.g. on the minimum wall thickness of the sheath 10, the size of a through channel 27 in a wall of the tubular body (cf. FIG. 2), or the size of the supply catheter 40 (cf. FIG. 3).

The sheath 10 comprises an expansion device in the form of an expansion sheath 26 displaceable on the base sheath 20 in the direction R of the vessel aperture. In the present example the expansion sheath 26 is configured as an expansion sheath 26 tubularly encompassing the base sheath 20. The expansion sheath 26 is adapted to be displaced on the base sheath 20 in the direction R in order to increase the outer diameter d of the sheath in the region of the place of entry G into the vessel when the sheath 10 has been inserted into the vessel. An outer diameter D thereafter present in the region of the vessel aperture exceeds the original outer diameter d by the amount 2x, where 2x can be as large as 0.75*d.

The sheath 10 comprises a sleeve 28. The latter is preferably fastened at its distal end to the base sheath 20 and can furthermore be fastened at its proximal end to the fixation element 60. The sleeve 28 encases the base sheath 20 and the expansion sheath 26 such that the expansion sheath 26 is displaceable on the base sheath 20 between the base sheath 20 and the sleeve 28. In this way a traumatic effect of the expansion sheath 26 on the vessel can be prevented and sterility is maintained when the expansion sheath 26 is displaced along the base sheath 20 into the vessel aperture in order to increase the outer diameter of the sheath 10 in the vessel aperture.

A wall 25 of the tubular body of the base sheath 20 has a through channel 27. The latter extends in the wall 25 from the proximal end 20b to the distal end 20a of the base sheath separately from the pass-through channel 22 of the base sheath 20 and preferably parallel to the pass-through channel 22. According to another embodiment (not shown), the through channel 27 is not separate from the pass-through channel 22 on its entire length, but e.g. only on the proximal end. On the distal end, the through channel 27 can form a sideways extension of the pass-through channel 22. The through channel 27 is adapted to conduct blood from the vessel (for example an artery) to the proximal end of the sheath 10 as soon as the sheath 10 has been inserted deep enough into the vessel. In this way a sufficient penetration depth into the vessel can be ascertained by means of the channel 27 in a simple manner.

In addition, the sheath 10 can include an externally readable marked region in an area of the sheath, which, in operation, is intended to be located in the area of the vessel puncture site. External readability can e.g. be achieved by providing the region with radiopaque markers. Also fluorogenic or echogenic substances can be used for forming the markers. This region can, according to a first embodiment, which is shown in FIGS. 2 and 3, be defined by two limiting markers 29a and 29b. These markers further guide the expansion and help locate the correct position of the sheath in relation to the distal opening of through channel 27 and the vessel puncture site thereof. Respective markers can e.g. be provided on the sleeve 28 covering the base sheath 20 and on the base sheath 20. Alternatively, it is possible to essentially uniformly mark the entire region by adding suitable externally readable substances to the sheath material in that region. According to such an embodiment, at least part of an expanding portion, such as the above-mentioned flexible portion and/or stretchable portion of the sheath, can be marked.

Further components of the sheath 10 will hereinafter be described with reference to FIG. 3, which shows the sheath 10 in a perspective view.

The channel 27 can be connected via a suitable connection 32, 55 to different measuring devices, for example a blood pressure measuring device 30. Alternatively or additionally, a temperature measuring device, for example a thermistor (not shown), can be connected to or inserted through the channel 27, for example in order to obtain information for the measurement of a patient's cardiac output.

Via the channel 27 a guidewire 50 can further be inserted into the vessel. An access to the channel 27 can be created for example via a Luer connector 55.

As mentioned above, the sheath 10 is suited to be guided via a supply catheter 40 of a heart pump 70. The heart pump 70, having the catheter 40, and the sheath 10 can be provided as a cohesive unit. The heart pump 70 is preferably introduced into the patient's vascular system here in the above-described manner by means of an introducing sheath which is removed using the peel-away technique and replaced by advancing the sheath 10.

The above-mentioned fixation element 60 serves for fixing, for example stitching, the sheath 10 to the patient after insertion of the sheath into a vessel of the patient. For this purpose, openings 66 can be provided. The fixation element 60 possesses an area 62 spanning the base sheath 20 for applying a sterile cover (not shown). The area 62 of the fixation element 60 slopes down in a ramp shape on both sides of the base sheath 20 transversely to the principal direction of the base sheath. Further, the fixation element 60 comprises a guide element 64 which serves as a stop for applying the sterile cover.

The fixation element 60 may further comprise circulation openings 67 and/or circulation opening slots (not shown) in order to allow for air circulation under the sterile cover. These openings or slots pass through the fixation element preferably in the direction in which the sheath passes through.

What is claimed is:

1. A sheath assembly for producing a fully sealed access to an interior of a vessel of an animal body or a human body, comprising:

a base sheath having a tubular body with a distal end and a proximal end, the tubular body defining a pass-through channel, with the base sheath being configured to be inserted into the vessel through a vessel aperture, a hemostatic valve, and an expansion sheath, wherein, with the base sheath disposed through the vessel aperture and in a stationary position in the vessel, the expansion sheath is displaceable on the base sheath in a direction of the vessel aperture to increase an outer diameter of the sheath assembly in a region of the vessel aperture, wherein a wall of the tubular body of the base sheath has a through channel extending inside of the wall from the distal end towards the proximal end, and wherein the through channel is open at the distal end and configured to conduct blood from the vessel towards the proximal end of the base sheath, allowing a sufficient penetration depth of the sheath assembly into the vessel to be ascertained.

2. The sheath assembly according to claim 1, wherein the through channel is present separately from the pass-through channel of the base sheath.

3. The sheath assembly according to claim 1, wherein the through channel is separate from the pass-through channel at the proximal end and not separate from the pass-through channel at the distal end.

4. The sheath assembly according to claim 1, further comprising a blood pressure measuring device which is connected to the through channel.

5. The sheath assembly according to claim 1, further comprising a temperature measuring element connected to or inserted through the through channel.

6. The sheath assembly according to claim 1, wherein the through channel is configured such that blood from a patient can be taken through the through channel.

7. The sheath assembly according to claim 1, comprising a guidewire which is introducible into the vessel from the proximal end of the base sheath through the through channel.

8. The sheath assembly according to claim 1, comprising a sleeve which encases the base sheath and the expansion sheath such that the sleeve is in contact with the vessel aperture in the stationary position of the sheath assembly in the vessel, and that the expansion sheath is displaceable on the base sheath between the base sheath and the sleeve.

9. The sheath assembly according to claim 1, wherein the expansion sheath is configured to increase the outer diameter of the sheath assembly in the region of the vessel aperture by at least 0.33 mm to 1.0 mm.

10. The sheath assembly according to claim 1, wherein the sheath assembly includes an externally readable marked region in an area of the sheath assembly, which, in operation, is intended to be located in the area of the vessel aperture.

11. The sheath assembly according to claim 1, comprising a fixation element for fixing the sheath assembly to a patient, with the fixation element having a surface with an area spanning the base sheath for applying a sterile cover, with the area sloping down in a ramp shape on both sides of the base sheath transversely to a principal direction of the base sheath, the principal direction extending from the proximal end to the distal end of the base sheath.

12. The sheath assembly according to claim 11, wherein the fixation element comprises a stop for applying the sterile cover, said stop extending at the proximal end of the area transversely to the principal direction of the base sheath.

13. The sheath assembly according to claim 1, comprising a heart pump having a supply catheter, with the base sheath being configured to be arranged displaceably on the supply catheter.

14. The sheath assembly according to claim 13, wherein the heart pump is configured to be displaced through the base sheath.

15. The sheath assembly according to claim 1, wherein the through channel is configured to conduct blood from the vessel towards the proximal end of the base sheath when a sufficient penetration depth of the sheath assembly into the vessel has been achieved.

16. The sheath assembly according to claim 1, wherein the hemostatic valve terminates the base sheath at the proximal end of the base sheath.

17. A sheath assembly for producing a fully sealed access to an interior of a vessel of an animal body or a human body, comprising:

a base sheath having a tubular body with a distal end and a proximal end, the tubular body defining a pass-through channel, with the base sheath being configured to be inserted into the vessel through a vessel aperture, a hemostatic valve, an expansion device configured to cooperate with the base sheath such that an outer diameter of the sheath assembly increases in a region of the vessel aperture with the sheath assembly in a stationary position in the vessel and upon actuation of the expansion device, and a sleeve which encases the base sheath and the expansion device, where the sleeve is configured to contact the vessel aperture in the stationary position of the sheath assembly in the vessel, wherein a wall of the tubular body of the base sheath has a through channel extending inside of the wall from the distal end towards the proximal end, and wherein the through channel is open at the distal end and configured to conduct blood from the vessel towards the proximal end of the base sheath, allowing a sufficient penetration depth of the sheath assembly into the vessel to be ascertained.

18. A sheath assembly for producing a fully sealed access to an interior of a vessel of an animal body or a human body, comprising:

a base sheath having a tubular body with a distal end and a proximal end, the tubular body defining a pass-through channel, with the base sheath being configured to be inserted into the vessel through a vessel aperture, a hemostatic valve, and a fixation element for fixing the sheath assembly to a patient, with the fixation element having a surface with an area spanning the base sheath for applying a sterile cover, with the area sloping down in a ramp shape on both sides of the base sheath transversely to a principal direction of the base sheath, the principal direction extending from the proximal end to the distal end of the base sheath, wherein a wall of the tubular body of the base sheath has a through channel extending inside of the wall from the distal end towards the proximal end, and wherein the through channel is open at the distal end and configured to conduct blood from the vessel towards the proximal end of the base sheath, allowing a sufficient penetration depth of the sheath assembly into the vessel to be ascertained.

19. The sheath assembly according to claim 18, wherein the fixation element comprises a stop for applying the sterile cover, said stop extending at the proximal end of the area transversely to the principal direction of the base sheath.

* * * * *